United States Patent [19]

Krasnicki et al.

[11] Patent Number: 4,930,507
[45] Date of Patent: Jun. 5, 1990

[54] DOUBLE CHAMBER ACOUSTICAL TONOMETER

[75] Inventors: Edward J. Krasnicki, Skaneateles, N.Y.; Donald L. Margolis, Davis, Calif.

[73] Assignee: Welch Allyn, Inc., Skaneateles Falls, N.Y.

[21] Appl. No.: 248,148

[22] Filed: Sep. 23, 1988

[51] Int. Cl.$^5$ .................................................. A61B 8/10
[52] U.S. Cl. ..................................... 128/649; 128/739; 128/774
[58] Field of Search .............................. 128/645–652, 128/745, 661.06, 676, 739, 774, 773; 73/78–79, 645–648, 573

[56] References Cited

U.S. PATENT DOCUMENTS

| | | | |
|---|---|---|---|
| 3,070,087 | 12/1962 | Sittel | 128/649 |
| 3,192,765 | 7/1965 | Keiper | 128/645 |
| 3,308,653 | 3/1967 | Roth | 128/645 |
| 3,613,666 | 10/1971 | Hobbs . | |
| 3,763,696 | 10/1973 | Krakau | 128/645 |
| 4,192,317 | 3/1980 | Munnerlyn et al. . | |
| 4,217,912 | 8/1980 | Hubmann et al. | 128/739 X |
| 4,771,792 | 9/1988 | Seale | 128/774 |

OTHER PUBLICATIONS

Hamelink et al.; "Ocular Tonometry Through Sonic Excitation and Laser Doppler Velocimetry"; *Journal of Biomech. Engineering*, vol. 101, 11-1979, pp. 261–270.
Survey of Ophthalmology, vol. 24, No. 4, Jan.–Feb. 1980, pp. 211–217.

*Primary Examiner*—Angela D. Sykes
*Attorney, Agent, or Firm*—Wall and Roehrig

[57] ABSTRACT

An acoustical tonometer having an ocular chamber in which a target eye is positionable, a drive chamber containing an acoustical generator and an inertia tube connecting the two chambers. Sound waves produced in the drive chamber are used to excite the target eye. The behavior of the eye on the resonant response of the system is used to determine the health of the eye.

17 Claims, 1 Drawing Sheet

U.S. Patent   Jun. 5, 1990   4,930,507
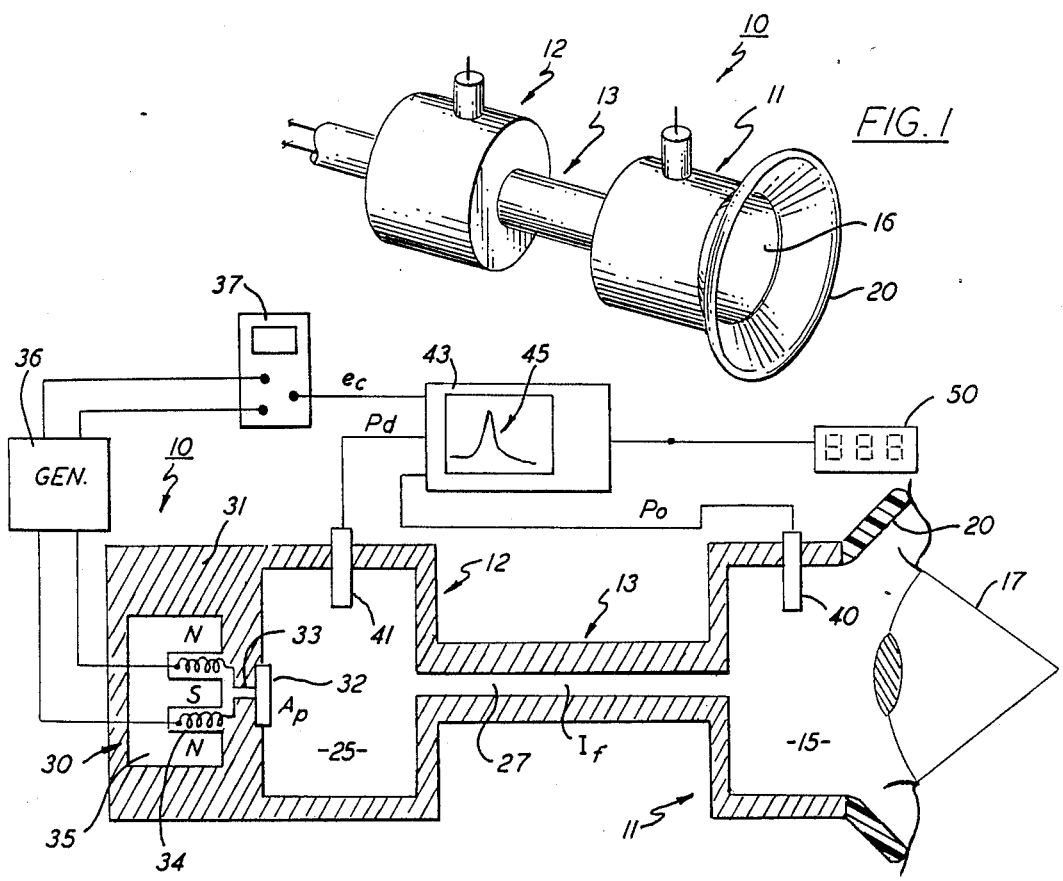
FIG. 1
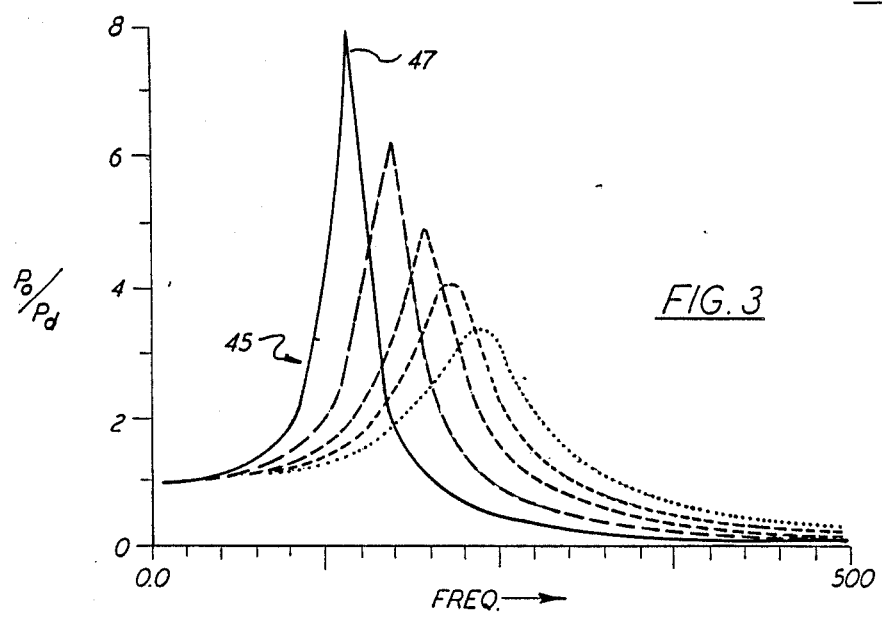
FIG. 2
FIG. 3

DOUBLE CHAMBER ACOUSTICAL TONOMETER

BACKGROUND OF THE INVENTION

This invention relates to tonometry and, in particular, to a non-contact tonometer for determining intraocular pressure and thus the health of a human eye.

Tonometry broadly relates to measuring tension in living tissue and has come to have special meaning in ophthalmology where it relates more specifically to intraocular pressure from which the health of the eye can be determined. Pressure within a living eye cannot be measured directly and has heretofore been inferred by measuring the eyes response to some external force. One of the most widely employed test in the art is the Goldmann applanation test wherein the cornea of the eye is flattened by a probe having a planar contact surface. The cornea is depressed until such time as a given radius is formed at the mouth of the depression. The force required to produce this depression is measured and intraocular pressure is inferred from the measurement. By testing a large number of subjects over a relatively long period of time, reasonable standards have been established so that diseased or glaucomatous eyes are now readily identified.

The Goldmann applanation test, and other similar tests, require that the test instrument physically touch and deform the cornea thereby increasing the risk of infection and the possibility of the cornea becoming abraded or otherwise damaged. Because of the risk involved, these contact tests must be conducted by a physician or a trained clinical technician. It is also common practice to anesthetize the patient when carrying out these contact tests in order to minimize patient discomfort and unwanted head movement. The use of anesthesia, however, sometimes produces an adverse effect in the patient and, because the patient is unable to feel normal pain, actually increases the risk of the damage.

The reliability of applanation test results are sometimes adversely effected by a number of uncontrollable variables. These include the size and shape of the patients eye, the amount of aqueous humor escaping from the eye as the cornea is being compressed, variations in the response of the sclera to the applied pressures, and the unwanted movement of the patient's head during testing. Attempts to correct or compensate test results for these uncontrolled variables have met with only limited sucess. Furthermore, because the applanation test requires that the instrument physically contact and depress the cornea, potentially harmful micro organisms can enter the patient's body through eye fluids if the contacting surface of the instrument is not carefully cleansed.

Lechtenstein, et al. in U.S. Pat. No. 3,545,260 discloses an eye test wherein corneal compliance is used to describe intraocular pressure. In this particular test, the eye is sealed within a gas filled chamber and the gas pressurized to a level sufficient to deform the cornea. The depth of depression created by the gas is measured using energy waves. Here again, the cornea of the eye must be deformed to obtain an indication of its health. Accordingly, the test poses a certain amount of danger and can only be repeated at safe intervals. In addition, it is extremely difficult to obtain and maintain a tight gas seal around the eye. Failure of the seal produces erroneous test results.

A later issued Lechtenstein et al. Pat. No. 3,690,158 discloses another test in which acoustical energy is used to measure the impedance of a patient's eye and thus provide information concerning intraocular pressure. Acoustical waves are directed through a liquid medium at both the patient's eye and a dummy target that has been arranged to simulate the behavior of a healthy eye. The acoustical impedance of the patient's cornea is measured by comparing the energy it reflects with the energy reflected by the dummy target through the liquid medium. The two impedances are then compared and any slight differences between the two provides indication as to condition of the eye. It is extremely difficult to keep a human eye sealed within the liquid medium and any movement or displacement of liquid will have an adverse effect on the test results. Accordingly, this type of testing has not found wide acceptance in the industry.

SUMMARY OF THE INVENTION

It is therefore an object of the present invention to improve tonometry.

A still further object of the present invention is to provide a small hand-held tonometer that is simple to operate and can be used by an untrained person to take intraocular measurements.

It is yet another object to the present invention to eliminate the use of corneal contact probes and topical anesthesia when measuring the eye for intraocular pressure thereby avoiding problems associated with corneal abrasion and the spread of infection.

Another object of the present invention is to provide a double chamber acoustical tonometer having a low frequency response that avoids many problems associated with high frequency acoustical measuring systems.

Yet another object of the present invention is to provide an acoustical tonometer that can accurately measure the resonant response of a human eye without being corrupted by outside influences.

These and other objects of the present invention are obtained by means of an acoustical tonometer that includes a first drive chamber acoustically connected to a second ocular chamber by means of a inertia tube. The ocular chamber has an opening in which the target (eye) is positioned and a dynamic seal that surrounds the eye to prevent loss of acoustical energy. An acoustical generator is placed in the drive chamber for producing acoustical waves over a desired range of frequencies. A first pressure transducer is mounted in the drive chamber while a second pressure transducer is similarly mounted in the ocular chamber for measuring changes in pressure over the frequency range.

In the main embodiment of the invention the pressure in the two chambers is compared and a plot of the compared values over the frequency range is generated to provide a peak response frequency that is related directly to the resonant response of the eye. By comparing the sensed pressures in the two chambers, the corrupting influence of the driver dynamic on the response curve are eliminated as well as other unwanted influences. In a second form of the invention the response curve is generated by comparing the sensed pressure on one chamber, either the ocular or the drive chamber, with driver voltage over the desired frequency range.

DESCRIPTION OF THE DRAWINGS

For a better understanding of these and other objects of the present invention, reference is made to the following detailed description of the invention which is to read in conjunction with the accompanying drawings, wherein:

FIG. 1 is a perspective view of a double chamber tonometer embodying the teachings of the present invention;

FIG. 2 is a enlarged schematic view of the tonometer shown in FIG. 1; and

FIG. 3 is a curve showing the resonant response produced by a human eye being tested by the present instrument.

DETAILED DESCRIPTION OF THE PREFERRED EMBODIMENT

Turning now to the drawings, a double chamber acoustical tonometer 10 embodying the teachings of the present invention is shown in perspective in FIG. 1 and in enlarged section in FIG. 2. The instrument includes a front housing 11 and a rear housing 12 that are joined by a narrow, hollow inertia tube 13. The front housing contains an ocular chamber 15, the distal end of which is open to provide an unobstructed circular window 16 which allows a target eye 17 to be positioned within the chamber. A dynamic seal 20 surrounds the window and protrudes outwardly from the housing 11. The seal is preferably formed of a soft pliable material that can be seated comfortably against the bony tissue surrounding the eye and pressed into conformity therewith to create an acoustical or dynamic seal that prevents energy waves contained within the ocular chamber from escaping. The seal may be contoured to better conform to the shape of the bony tissue surrounding the eye to provide for a more secure seal.

The rear housing 12 contains a second drive chamber 25. As best illustrated in FIG. 2, the drive chamber communicates with the ocular chamber through means of the noted inertia tube 13. The inertia tube has a central bore 27 that passes between the drive chamber and the ocular chamber, the function of which will be explained in greater detail below.

An acoustical generator, generally referenced 30 is mounted in the back wall 31 of the rear housing for producing sound waves in drive chamber 25. In this particular embodiment of the invention, the generator includes a piston 32 that is coupled by means of an arm 33 to an electrical coil 34 which is surrounded by a permanent magnet 35. The coil is excited by means of a frequency generator 36 so that the piston is caused to vibrate linearly through a predetermined range of frequencies thereby producing pressure fluctuations within the drive chamber. In practice, the acoustical generator can be either a wide band noise generator or a sweep generator that is selectively tuned to sweep across a desired range of frequencies. In operation, the generator produces acoustical fluctuations within the drive chamber which, in turn set up oscillations in the inertia tube. These oscillations are transmitted through the inertia tube to the ocular chamber where they are used to excite a target eye sealed within the window of the ocular chamber. The resonant response of the eye will thus have a direct effect on the overall resonant response of the system. As will be explained in greater detail below, the resonant response of the system can be measured in a number of ways to provide valuable information concerning the compliance or the stiffness of the eye.

In the main embodiment of the invention, the changes in pressure within both the drive and ocular chambers over the given frequency range is used to determine the resonant response of the instrument. Pressure fluctuations within the chambers are sensed by means of transducers 40 and 41 mounted in the top of housings 11 and 12, respectfully. The pressure sensors are connected to an analyzer 43 by means of appropriate input lines. In addition, the voltage over the signal generator is fed to the analyzer through a voltage sensor 37 to provide the analyzer with both pressure and voltage information as it sweeps over the desired frequency range. In the preferred embodiment of the invention the sensed pressures in the ocular chamber (Po) and the drive chamber (Pd) are compared (Po/Pd) over the frequency range to provide a resonant response curve 45 that accurately reflects the behavior of the eye. This curve is presented on the screen of the analyzer. Through appropriate circuit means, the frequency at which the peak resonant frequency occurs is presented by the digital read out window 50.

The resonant response curve 45 for the instrument is shown in greater detail in FIG. 3. As noted, the curve is generated by plotting Po/Pd valves over the desired low frequency range which is preferably 0 and 500 Hz. As can be seen, the curve has a single clearly discernable spike that peaks at some frequency. The frequency at which the curve peaks is directly related to the resonant frequency of the target eye. A healthy, more compliant, eye will cause the curve to peak at relatively low frequencies while a stiffer, less compliant eye, will cause the curve to peak at higher frequencies. By conducting a number of tests on both healthy and glaucomic eyes, a band of frequencies in which the resonant frequency of a healthy eye peaks can be readily identified. Just as importantly, the onset of an unhealthy condition can be also detected by noting the shift of the eyes peak response from the lower frequencies toward the higher frequencies. This shift in response for a healthy eye to a unhealthy response is depicted by the dotted line curves shown in FIG. 3. Because the present test does not require the eye to be physically deformed by the instrument, it can be repeated at very short intervals without causing harm to the patient. Accordingly, a history of the eyes behavoir can be obtained in relatively short period of time.

By comparing the changes in pressure in the drive chamber with pressure changes in the ocular chamber, the resonant response curve produced over the desired frequency range will not be corrupted or adversely effected by unwanted driver dynamics. The instruments response is therefore primarily dependant upon its blocked end frequency response. The blocked end frequency response is the response produced by the instrument when the target window is blocked or closed by a rigid object such as a steel block. Through tests, it has been determined that extremely reliable eye compliancy readings are obtained when the blocked frequency response peak occurs somewhere between 50 and 100 Hz.

The instrument or system can be tuned to a desired blocked frequency response by changing the volume of the chambers and/or the bore size of the inertia tube. In the preferred embodiment of the invention, the volume of each chamber is about equal to that of the other and the volume of each chamber is about 2 to 3 times greater than that of the inertia tube bore. Although the inertia tube is shown as being straight in FIGS. 1 and 2, the tube can be wound into a coil to save space without adversely effecting the operation of the instrument.

Chamber pressures are the preferred values for use in determining the compliance of a target because use of these parameters eliminates unwanted driver dynamics and reading can be obtained at frequencies low enough so that other unknown eye properties are not a factor. Similar results have also been obtained by comparing a single chamber pressure to acoustical generator voltage over the test range. The curves generated using this type of pressure to voltage comparison are not as sharp when compared to those utilizing pressure to pressure value, however, the eye behaviorial patterns measured by the instrument remain the same so that accurate indications of intraocular pressures can be obtained.

While this invention has been described with reference to the structure disclosed herein, it is confined to the details set forth and this application is intented to cover any modifications or changes as may come within the scope of the following claims.

What is claimed is:

1. Apparatus for monitoring the resonant behavior of a in-vivo eye to determine the compliance of the eye that includes an enclosed ocular chamber having an unobstructed opening in which a target eye is positionable and an acoustical seal surrounding the opening, an enclosed drive chamber having an acoustical generator associated with said drive chamber to produce acoustical waves within the chamber over a given range of frequencies, an inertia tube connecting the two chambers whereby pressure fluctuations produced in the drive chamber are transmitted into the ocular chamber to excite the eye, a first sensor means in the ocular chamber for sensing the pressure in said ocular chamber, a second sensor means in the drive chamber for sensing the pressure in said drive chamber, and analyzer means connected to both sensor means for comparing the two chamber pressures over the given range of frequencies and providing an output indicative of the resonant response of the apparatus from which the compliance of the eye can be determined from the peak resonant response frequency.

2. The apparatus of claim 1 wherein the volumes of the two chambers and the inertia tube are arranged so that the blocked resonant frequency of the system occurs at between 50 and 100 Hz.

3. The apparatus of claim 2 wherein the volume of the chambers are about equal.

4. The apparatus of claim 3 wherein the volume of the chambers are between 2 and 3 times larger than the volume of the inertia tube.

5. The apparatus of claim 1 wherein said analyzer means includes means for plotting the compared pressures over the given frequency range.

6. The apparatus of claim 1 wherein said frequency range is between 0 and 500 Hz.

7. Apparatus for monitoring the resonant behavior of a human eye to determine the compliance of the eye that ihncludes an enclosed ocular chamber having an unobstructed opening in which a target eye is positionable and an acoustical seal surrounding the opening, an enclosed drive chamber having an acoustical generator associated therewith for producing sound waves within the drive chamber over a given range of frequencies, a inertia tube connecting the two chambers wherein sound waves produced in the drive chamber are transmitted to the ocular chamber to excite an eye positioned in said opening, a pressure sensor means positioned in one of the chambers for measuring the pressure in said chamber, voltage sensor means connected to the acoustical generator for monitoring the voltage over said generator, and analyzer means connected to the pressure and voltage sensor means for comparing the sensed pressure to the sensed voltage over said given frequency range and providing an output indicative of the resonant response of the system whereby the compliance of the target eye can be determined directly from the peak resonant response frequency.

8. The apparatus of claim 7 wherein said pressure sensor means is mounted in the drive chamber.

9. The apparatus of claim 8 wherein said pressure sensor is mounted in the ocular chamber.

10. The apparatus of claim 7 wherein the volumes of the two chambers and the volume of the inertia tube are related so that peak blocked resonant frequency of the system occurs at between 50 and 100 Hz.

11. The apparatus of claim 10 wherein the volumes of the two chambers are about equal.

12. The apparatus of claim 11 wherein the volume of each chamber is between 2 and 3 times the volume of the inertia tube.

13. A method of determining the compliance of the human eye that includes the steps of positioning an eye within an enclosed ocular chamber, connecting the ocular chamber with a second enclosed drive chamber by means of an inertia tube, producing sound waves in the drive chamber over a given range of frequencies whereby the eye in the ocular chamber is excited, measuring the frequency response of the system over the range of frequencies to determine the peak resonant frequency of the system, and relating the peak resonant frequency of the system to the compliance of the eye.

14. The method of claim 13 wherein the frequency response of the system is measured by comparing the pressures in both chambers over the range of frequencies.

15. The method of claim 13 that includes the step of tuning the system so that peak blocked resonant frequency of the system occurs at between 50 and 100 Hz.

16. The method of claim 13 wherein the sound waves are produced in the drive chamber by sweeping an acoustical generator over a range of frequencies between 0 and 500 Hz.

17. The method of claim 16 wherein the frequency response of the system is measured by comparing the pressure in one of the chambers with the voltage across the generator over the given frequency range.

* * * * *